United States Patent
Takagi

(10) Patent No.: US 10,139,363 B2
(45) Date of Patent: Nov. 27, 2018

(54) BHF SOLUTION CONCENTRATION MEASUREMENT DEVICE AND BHF SOLUTION CONCENTRATION MEASUREMENT METHOD

(71) Applicant: HORIBA, Ltd., Kyoto-shi, Kyoto (JP)

(72) Inventor: So Takagi, Kyoto (JP)

(73) Assignee: HORIBA, LTD., Kyoto-shi, Kyoto (JP)

( * ) Notice: Subject to any disclaimer, the term of this patent is extended or adjusted under 35 U.S.C. 154(b) by 170 days.

(21) Appl. No.: 15/242,315

(22) Filed: Aug. 19, 2016

(65) Prior Publication Data

US 2017/0059524 A1 Mar. 2, 2017

(30) Foreign Application Priority Data

Aug. 28, 2015 (JP) .................. 2015-169375

(51) Int. Cl.
*G01N 27/36* (2006.01)
(52) U.S. Cl.
CPC .................. *G01N 27/36* (2013.01)
(58) Field of Classification Search
None
See application file for complete search history.

(56) References Cited

U.S. PATENT DOCUMENTS

| 6,173,600 B1 * | 1/2001 | Harada | ................ G01N 27/286 |
| | | | 73/1.06 |
| 2009/0217756 A1 * | 9/2009 | Bagwell | .................. G01N 9/14 |
| | | | 73/440 |

FOREIGN PATENT DOCUMENTS

JP H08334461 A 12/1996

* cited by examiner

*Primary Examiner* — Eli S Mekhlin
(74) *Attorney, Agent, or Firm* — Alleman Hall Creasman & Tuttle LLP

(57) ABSTRACT

In order to make it possible to accurately measure the HF concentration in a BHF solution in a low concentration region using a simple structure, there are provided a relationship storage unit that stores relationships between a pH of a BHF solution and an HF concentration, a pH meter that measures the pH of the BHF solution, and a concentration calculation unit that refers to relationships stored in the relationship storage unit, and calculates the HF concentration from the pH values measured by the pH meter.

6 Claims, 3 Drawing Sheets

BHF SOLUTION CONCENTRATION MEASUREMENT DEVICE AND BHF SOLUTION CONCENTRATION MEASUREMENT METHOD

TECHNICAL FIELD

The present invention relates to a buffered hydrofluoric acid (BHF) solution concentration measurement device that measures a hydrofluoric acid (HF) concentration in buffered hydrofluoric acid that is used in a semiconductor device manufacturing process or the like, and to a BHF solution concentration measurement method.

TECHNICAL BACKGROUND

A buffered hydrofluoric acid solution (this may be referred to below as a BHF solution) is used, for example, in a semiconductor device etching process. Because the speed of this etching is determined by the concentration of the HF which is the principal constituent in the BHF solution, conventionally, as is shown, for example, in Patent document 1, the HF concentration is measured and controlled using an optical measurement device.

In recent times, in conjunction with the increasing miniaturization of semiconductor devices, an extremely low concentration BHF solution is sometimes used in which the HF concentration has been diluted to one tenth or one hundredth of the conventional concentration.

However, in the above-described conventional optical measurement device, it is difficult to accurately measure the HF concentration in a BHF solution in such a low concentration region.

DOCUMENTS OF THE PRIOR ART

Patent Documents

Patent document 1 Japanese Unexamined Patent Application (JP-A) No. 08-334461

DISCLOSURE OF THE INVENTION

Problems to be Solved by the Invention

The present invention was conceived in view of the above-described circumstances and it is an object thereof to make it possible to accurately measure the HF concentration in a BHF solution in a low concentration region using a simple structure.

Means for Solving the Problem

Namely, the BHF solution concentration measurement device according to the present invention measures an HF concentration in a BHF solution and is equipped with a relationship storage unit that stores relationships between a pH of a BHF solution and an HF concentration, a pH meter that measures the pH of the BHF solution, and a concentration calculation unit that refers to relationships stored in the relationship storage unit, and calculates the HF concentration from the pH values measured by the pH meter.

Specifically, a BHF solution is created by mixing $NH_4F$ and HF in water (additional substances may also be added to this mixture). The present inventors discovered that, when the BHF solution is in a low concentration (i.e., where the HF concentration is approximately between 1 ppm and 500 ppm), the pH is sensitive to the HF concentration, however, the pH is insensitive (i.e., it is reduced to less than one fiftieth of its sensitivity towards the HF concentration) to the $NH_4F$ concentration, and as a result were able to complete the present invention for the first time.

Note that, here, the pH value is a concept that also includes values that indirectly show the pH (for example, the concentration of $H^+$ and the like). The same applies to the HF concentration and the $NH_4F$ concentration.

According to this configuration, it is possible to accurately measure the HF concentration in a BHF solution simply by measuring the pH.

The present inventors also discovered that the relationship between the pH and the HF concentration changes depending on the $NH_4F$ concentration. According to this discovery, it is preferable for the relationship storage unit to store relationships between the pH and the HF concentration for each one of a plurality of different $NH_4F$ concentrations, and for the concentration calculation unit to refer to the relationship corresponding to a given $NH_4F$ concentration, and to calculate the HF concentration from the value of the pH measured by the pH measurement unit.

Because a BHF solution corrodes glass, it is difficult to consider using a glass electrode as the pH meter. However, in the case of the aforementioned low concentration BHF solution, it is possible to use a glass electrode and the HF concentration can be measured with excellent responsiveness.

A more specific example of the pH meter is a pH meter that is constructed so as to include a body that stores an internal liquid, and a tube that is formed either partially or wholly from response glass and through which the BHF solution flows, wherein the tube penetrates the body such that the response glass forming the tube is in contact with the internal liquid inside the body.

According to a structure of this type, by forming the tube such that it has a narrow diameter, only a small quantity of BHF solution is required for the sampling and there is no need to collect the BHF solution in a container. Because of this, the quantity of BHF solution that is used for a measurement can be reduced, and the quantity of BHF solution that is lost due to the measurement process can be dramatically reduced compared to a conventional structure. Moreover, because the tube is unaffected by any convection current in the BHF solution, the measurement accuracy can be improved.

Furthermore, if a structure is employed in which the flow of BHF solution through the tube is stopped while the concentration of the HF in the BHF solution is being measured, then it is possible to eliminate any effect on the measurement values that might be caused by the flow of the BHF solution.

Effects of the Invention

According to the present invention which is constructed in this manner, it is possible to accurately measure the HF concentration in the BHF solution. Moreover, because this HF concentration is calculated from the pH value, a complicated structure can be avoided.

LIST OF REFERENCE CHARACTERS

Figure 1:
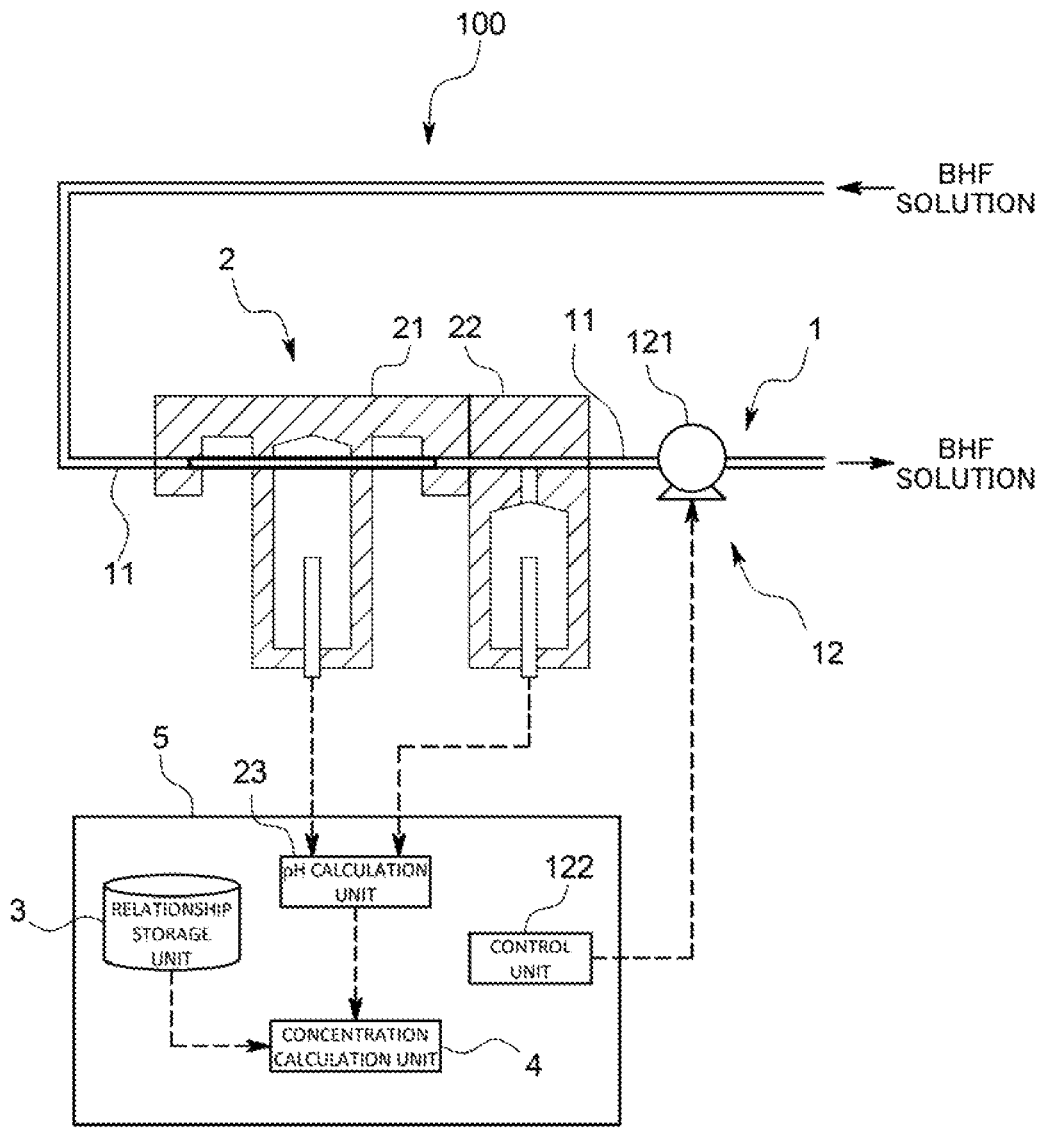
FIG. 1 is an overall typical view of a BHF concentration measurement device according to an embodiment of the present invention.

100 . . . BHF solution concentration measurement device
2 . . . pH meter
3 . . . Relationship storage unit
4 . . . Concentration calculation unit
211 . . . Body (First body)
212 . . . Tube
G . . . Response glass Embodiments for Implementing the Invention Hereinafter, an embodiment of the present invention will be described with reference made to the drawings. A BHF concentration measurement device 100 according to the present embodiment is used to measure an HF concentration in a BHF solution that is used, for example, in an etching process or the like during semiconductor manufacturing, and is incorporated as part of a semiconductor manufacturing apparatus production line.

This will now be described in detail.

As is shown in FIG. 1, this BHF concentration measurement device 100 is connected to a main flow path (not shown in the drawings) along which flows a BHF solution that is used for etching, and is equipped with a sampling mechanism 1 that samples a portion of the BHF solution, a pH meter 2 that measures a pH of the sampled BHF solution, a relationship storage unit 3 that stores relationships between the pH of the BHF solution and the HF concentration, and a concentration calculation unit 4 that refers to the relationships stored in the relationship storage unit 3, and calculates the HF concentration from the pH values measured by the pH meter 2.

The sampling mechanism 1 is equipped with a sampling flow path 11 that communicates with the main flow path, and a distribution control mechanism 12 that controls the introduction and the like of the BHF solution into the sampling flow path 11.

The sampling flow path 11 is a flow path along which sampled BHF solution flows, and is formed from a pipe component that is resistant to corrosion caused by the BHF solution.

The distribution control mechanism 12 is equipped with a pump 121 that is provided on the sampling flow path 11, and a control unit 122 that controls operations of the pump 121.

In this embodiment, the role of the control unit 122 is performed by an information processing circuit 5 that is provided separately from the pump 121. This information processing circuit 5 is equipped with a digital circuit that's is formed by a CPU, memory, and communication ports and the like, an analog circuit that is equipped with a buffer and an amplifier and the like, and an A/D converter and D/A converter and the like that intercede between the digital circuit and the analog circuit. As a result of the CPU and the peripheral devices thereof operating in collaboration with each other in accordance with a predetermined program that has been stored in the memory, this information processing circuit 5 demonstrates the functions of the control unit 122.

In this structure, when the pump 122 is operated as a result of a command signal from the control unit 122, a portion of the BHF solution flowing through the main flow path is drawn into the sampling flow path 11, and when the pump 121 stops, the sampling of the BHF solution is also stopped.

Here, the pH meter 2 calculates a pH based on what is known as a glass electrode method, and is equipped with a glass electrode 21 and a reference electrode 22, and with a pH calculation unit 23 that calculates a pH based on a potential difference between the respective electrodes 21 and 22.

Figure 2:
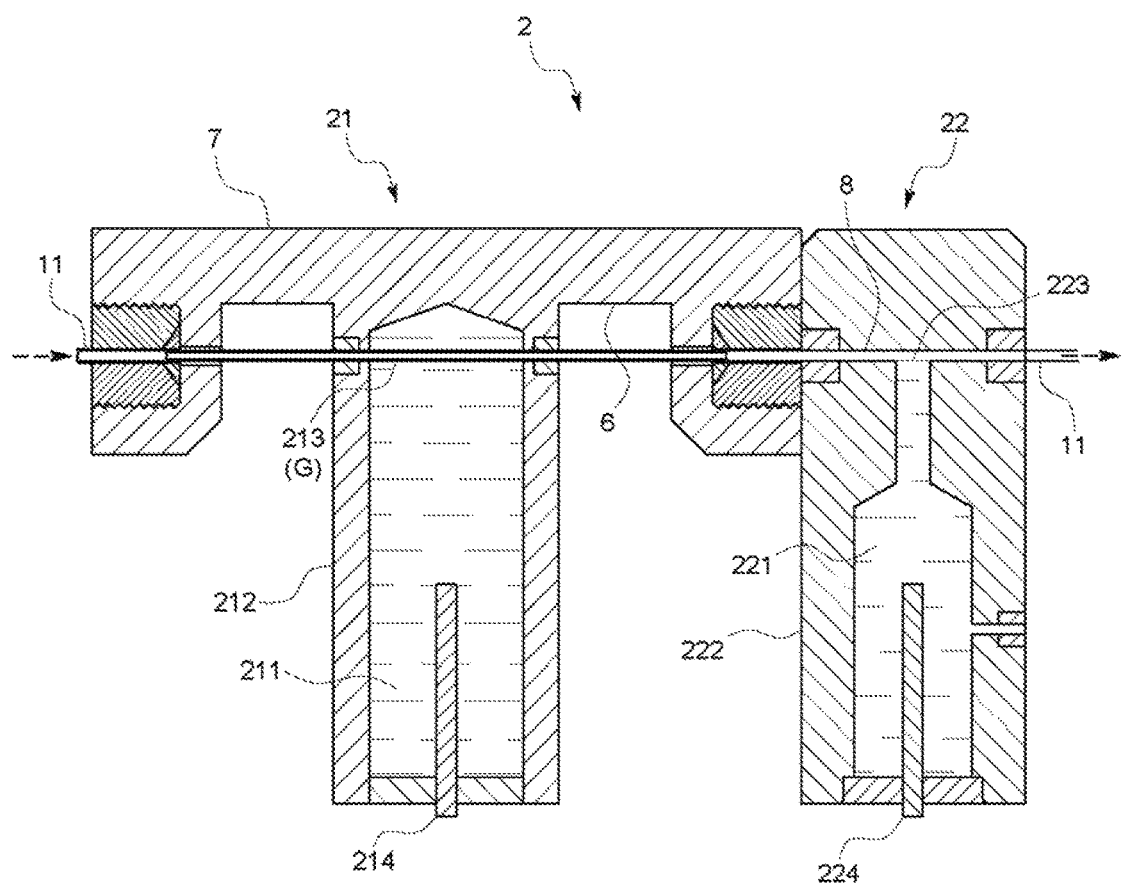
FIG. 2 is a cross-sectional view showing a pH meter of the same embodiment.

As is shown in FIG. 2, the glass electrode 21 is equipped with a first body 212 inside which a first internal liquid 211 is stored, response glass G that is provided in the first body 212, and a first internal electrode 214 that is immersed in the first internal liquid 211.

The first body 212 is shaped as a hollow block body that is formed from a material such as, for example, PVC (polyvinyl chloride), PP (polypropylene), and PVDF (polyvinylidene fluoride) and the like.

The first internal liquid 211 is, for example, a pH buffer solution or the like.

As is widely known, the response glass G is interposed between the first internal liquid 211 and the measurement subject which, in this case, is the BHF solution, and causes a potential to be generated by the pH difference between these. In this embodiment, a tube 213 is formed by this response glass G The tube 213 that is formed by this response glass G is extremely thin and is formed in a capillary shape. The tube 213 penetrates one side surface of the first body 212 and, after extending through the internal space, emerges from another side surface thereof. An internal diameter of the tube 213 is between, for example, approximately 0.1 mm and 2 mm, and is preferably between approximately 0.5 mm and 1 mm.

A starting end of this tube 213 is connected to the sampling flow path 11, and BHF solution is introduced from the main flow path into the tube 213 by the operation of the pump 121.

In this manner, while an exterior surface of the tube 213 is in contact with the first internal liquid 211 that fills the internal space, by introducing the BHF solution into the interior of the tube 213, as is described above, the response glass G (i.e., the tube 213) is interposed between the first internal liquid 211 and the BHF solution which is serving as the measurement subject.

Note that, in this embodiment, the entire tube 213 is formed by the response glass however, it is also possible for only the portion of the tube 213 that is in contact with the first internal liquid 211 to be formed from the response glass G The first internal electrode 214 is formed in a rod shape or in an elongated plate shape from, for example, silver/silver chloride, and is attached such that it penetrates a bottom wall of the first body 212 so that a portion thereof is immersed in the first internal liquid 211.

As is shown in FIG. 2, the reference electrode 22 is equipped with a second body 222 that internally stores a second internal liquid 221, a second internal electrode 224 that is immersed in the second internal liquid 221 and outputs a reference potential, and a liquid junction portion 223.

The second body 222 is shaped as a hollow block body that is formed from a material such as, for example, PVC (polyvinyl chloride), PP (polypropylene), and PVDF (polyvinylidene fluoride) and the like, and an interior space thereof is filled with the second internal liquid 221. This second internal liquid 221 is, for example, a pH buffer solution or the like.

In addition to the above-described internal space, an internal flow path 8 into which the BHF solution is introduced is also provided in the second body 222. This internal flow path 8 is a through hole that penetrates the second body 222 so as to extend from one side surface thereof across to another side surface thereof, and a starting end of the internal flow path 8 is in communication with a terminating end of the tube 213. By employing this structure, after the BHF solution has passed through the tube 213, it is introduced into the internal flow path 8. Note that this internal flow path 8 is also formed in a narrow-diameter capillary configuration in the same way as the tube 213.

The second internal electrode 224 is formed in a rod shape or in an elongated plate shape from, for example, silver/silver chloride, and is attached such that it penetrates a bottom wall of the second body 222 so that a portion thereof is immersed in the second internal liquid 221.

The liquid junction is formed in a contact portion where the internal flow path 8 comes into contact with the internal space.

More specifically, an internal diameter of the internal space is formed narrower on the upper side in the drawing of the area where the second internal electrode 224 is inserted, namely, at the end portion on the opposite side from the bottom wall. The internal space comes into contact with a side surface of the internal flow path 8 at a distal end of this narrow diameter portion. The liquid junction portion 223 is formed by providing either an extremely small hole or a porous component in this contact portion.

Furthermore, in this embodiment, the first body 212 and the second body 222 are disposed apart from each other such that side surfaces thereof are mutually facing each other, and the first body 212 and the second body 222 are integrally connected to each other by a spacer component 6. A terminating end portion of the tube 213 protrudes from the side surface of the first body 212 in a location that is offset from the spacer component 6, and this protruding end is connected to the starting end of the internal flow path 8 of the second body 222.

The reason why the protruding end of the tube 213 is exposed to the external space in this manner is so that, even if the first internal liquid 211 leaks from the gap between the tube 213 and the first body 212 due to some unforeseen circumstance, the first internal liquid 211 is prevented from reaching the interior of the second body 222.

For the same reasons, the starting end portion of the tube 213 is also made to protrude from the first body 212 so as to be exposed to the external space. The symbol 7 in the drawing is a supporting component that supports the starting end portion of the protruding tube 213.

As is shown in FIG. 1, the pH calculation unit 23 measures a potential difference between the first internal electrode 214 and the second internal electrode 224, and calculates the pH of the BHF solution based on this potential difference. In this embodiment, the information processing circuit 5 operates in collaboration with the CPU and peripheral devices in accordance with a predetermined program that has been stored in the memory, and demonstrates the functions of the pH calculation unit 23.

The relationship storage unit 3 stores relationships between the pH value of the BHF solution and the HF concentration for each concentration of $NH_4F$ and, physically, is set in a predetermined area of the memory of the information processing device.

Figure 3:
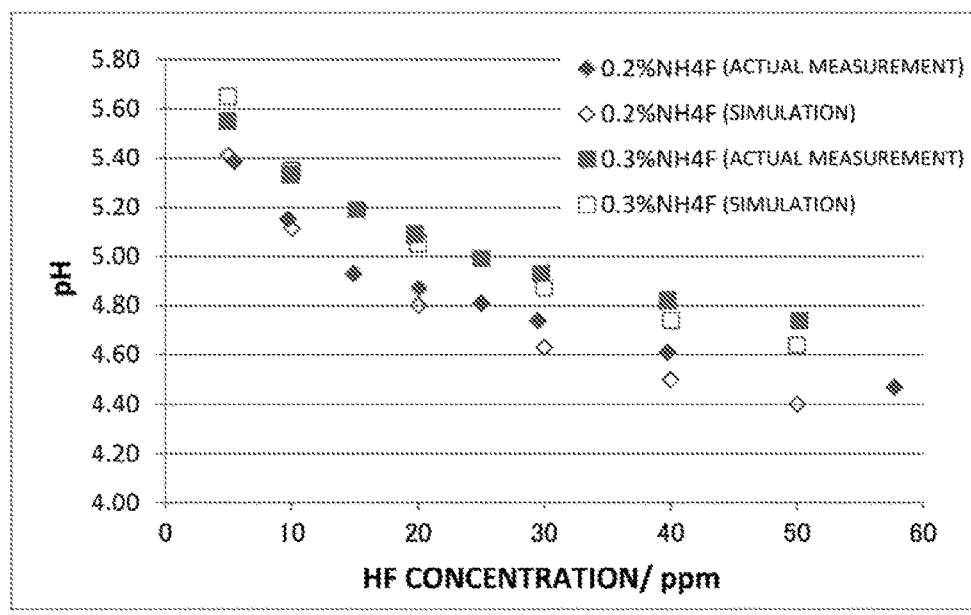
FIG. 3 is a graph showing the results when the pH concentration and the HF concentration are in a relationship of 1:1, and this relationship changes depending on the $NH_4F$ concentration in the same embodiment.

These relationships were first discovered by the present inventors, and have been determined in advance, for example, by experiments. FIG. 3 is a graph showing the results when the relationships were determined by experiments for $NH_4F$ concentrations of both 0.2% (2000 ppm) and 0.3% (3000 ppm). These relationships are stored in advance in the relationship storage unit 3 as lookup tables and calculation formulas.

Note that the present inventors consider that the reasons why these relationships are established are as follows.

It is known that each component of the BHF solution dissociates in the following manner. Here, K is a dissociation constant.

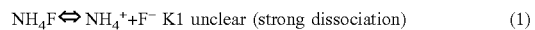

$$NH_4F \Leftrightarrow NH_4^+ + F^-  \quad K1 \text{ unclear (strong dissociation)} \tag{1}$$

$$HF \Leftrightarrow H^+ + F^-  \quad K2 = 1.3*10^{-3} \tag{2}$$

$$HF_2^- \Leftrightarrow H + F^-  \quad K3 = 0.104 \tag{3}$$

If it is assumed that the $NH_4F$ is completely dissociated, and if the initial concentration of the HF that was added when the BHF solution was prepared is taken as H, the initial concentration of the $NH_4F$ is taken as N, the concentration of the $H^+$ is taken as C, and the concentration of the $HF_2^-$ is taken as D, then when a state of equilibrium is attained, the final $F^-$ concentration can be expressed as N+C−D, and the final HF concentration can be expressed as H−C−D. Here, because the dissociation constants of Formulas (2) and (3), the initial concentration (H) of the HF, and the initial concentration (N) of the $NH_4F$ are already known, if the value of the $H^+$ concentration (C), namely, the value of the pH is ascertained, then the HF concentration can be calculated from this value and from the Formulas (2) and (3). Because of this, it can be said that a 1:1 relationship that can be expressed by a particular constant mathematical formula is established between the pH value of the BHF solution and the HF concentration. Simulated results obtained on the basis of this formula are shown in FIG. 3. It can be seen that the same trend as was obtained from the experiment results is evident.

What can be said about the above-described formula is that a 1:1 relationship exists between the HF concentration before the dissociation was generated (for example, as was described above, the concentration of HF that was added when the BHF solution was prepared) and the HF concentration when a state of equilibrium was attained. Accordingly, the HF concentration referred to in the present invention may be either one of these.

The concentration calculation unit 4 acquires the pH values measured by the pH meter 2, and calculates HF concentrations from the measured pH values by referring to the relationships stored in the relationship storage unit 3. The information processing circuit 5 performs the role of this concentration calculation circuit 4 as a result of the CPU and the peripheral devices operating in collaboration with each other in accordance with a predetermined program stored in the memory.

Because the relationships stored in the relationship storage unit 3 differ for each $NH_4F$ concentration, the $NH_4F$ concentration is also necessary for the calculation of the HF concentration. Here, an operator, for example, uses values input prior to the process. It can be seen from the experiment results shown in FIG. 3, or from simulation results that the relationship changes slightly when the $NH_4F$ concentration varies 0.1% (1000 ppm), however, this is because, during the etching process, there is substantially no occasion when the $NH_4F$ concentration varies to this extent.

Next, an example of an operation of the BHF concentration measurement device 100 that is constructed in the manner described above will be described simply.

Firstly, the control unit 122 issues a command to the pump 121 which causes the BHF solution to be sampled from the main flow path. After the BHF solution has filled the tube 213 of the glass electrode 21 and the internal flow path 8 of the reference electrode 22, the pump 121 is stopped so that the flow of BHF solution is halted. In this state, the concentration of HF in the BHF solution is measured. After this measurement has ended, the connection destination of the sampling flow path 11 is switched to a cleaning solution tank (not shown in the drawings) by operating a valve (also not shown in the drawings) or the like, and the BHF solution in the sampling flow path 11 is purged. The HF concentration in the BHF solution is successively measured by repeating this series of actions at a predetermined timing.

In this manner, according to the BHF concentration measurement device 100 having the above-described structure, the following effects are achieved.

As is shown in the graph in FIG. 3, it can be seen that, even if the HF concentration varies by several ppm, the pH value reacts sensitively to that. Compared to this, the pH value only reacts extremely dully to variations (1000 ppm) in the $NH_4F$ concentration. Accordingly, in a low concentration region (i.e., where the HF concentration is approximately between 1 ppm and 500 ppm and, preferably, between 5 ppm and 50 ppm) where it has not hitherto been possible to make measurements using a conventional concentration meter, the HF concentration can be measured precisely at a resolution in the order of ppm. Moreover, because only the pH meter 2 is used for this measurement, the measurement structure does not become any more complex.

Because the tube 213 has a narrow diameter, the quantity of BHF solution that is used in the measurement can be kept extremely small. Accordingly, the quantity of BHF solution that is lost is dramatically lower compared to a conventional structure, and because of the narrow diameter, the tube 213 is unaffected by any convection current in the BHF solution and the measurement accuracy can be improved.

Because the glass electrode 21 is used as the pH meter 2, the measurement can be performed in a short time span. Because of this, it is possible, for example, to monitor the HF concentration in the BHF solution in the etching step essentially in real time.

In contrast, because only a minute sampling quantity of BHF solution is required for the measurement thereof, in combination with the fact that the BHF solution has an extremely low HF concentration, damage that is caused by corrosion and the like to the glass electrode 21 can be kept to a bare minimum, and the device lifespan can be made long enough for it to withstand a long period of use.

Because the sampling flow path 11 is purged each time a measurement is made, this fact also contributes to the decrease in damage to the glass electrode 21.

Note that the present invention is not limited to the above-described embodiment.

For example, relationships are stored discretely for each $NH_4F$ concentration in the relationship storage unit, however, if, the relationships for the $NH_4F$ concentration in that BHF solution being used is not stored in the relationship storage unit, but is instead, for example, an intermediate value between two relationships, then the relationship can be determined by interpolation from these two relationships on either side.

The shape of the pH meter may be that of a rod-shaped glass electrode, while, functionally, a pH meter that is able to withstand hydrofluoric acid may be used. A pH meter without any special functions may be used, and one that is not a glass electrode may also be used. In the above-described embodiment, initial values input by an operator are used for the concentration of the $NH_4F$, however, it is also possible to provide a separate $NH_4F$ concentration meter (for example, measurements may also be made by means of a conductivity meter or an absorption spectrometer), and to acquire values from this meter. In the present embodiment, the $NH_4F$ concentration is used as a parameter for a relational formula to convert from a pH concentration to an HF concentration, however, in addition to this it is also possible to consider the temperature and the voltage.

Additionally, the present invention is not limited to the examples shown in the drawings, and various modifications and the like may be made insofar as they do not depart from the spirit or scope of the present invention.

What is claimed is:

1. A buffered hydrofluoric acid (BHF) solution concentration measurement device that measures a hydrofluoric acid (HF) concentration in a BHF solution comprising at least ammonium fluoride ($NH_4F$) and HF in water, the BHF solution concentration measurement device comprising:
   a relationship storage unit, executed on a processor, that stores relationships between a pH of the BHF solution and an HF concentration based on the $NH_4F$ concentration of the BHF solution;
   a pH meter, including a first electrode and a reference electrode, that measures the pH of the BHF solution; and
   a concentration calculation unit, executed on the processor, that refers to the relationships stored in the relationship storage unit, and calculates the HF concentration from pH values measured by the pH meter, wherein
   the HF concentration in the BHF solution is between 1 part-per-million (ppm) and 500 ppm.

2. The BHF solution concentration measurement device according to claim 1, wherein the relationship storage unit stores relationships between the pH and the HF concentration for each one of a plurality of different $NH_4F$ concentrations, and
   the concentration calculation unit refers to the relationship corresponding to a given $NH_4F$ concentration, and calculates the HF concentration from the value of the pH measured by the pH meter.

3. The BHF solution concentration measurement device according to claim 1, wherein the first electrode is a glass electrode.

4. The BHF solution concentration measurement device according to claim 3, wherein the glass electrode of the pH meter further comprises:
   a body that stores an internal liquid; and
   a tube that is formed either partially or wholly from response glass, and through which the BHF solution flows, and wherein
   the tube penetrates the body such that the response glass forming the tube is in contact with the internal liquid inside the body.

5. The BHF solution concentration measurement device according to claim 4, further comprising a pump, wherein, when the concentration of the HF in the BHF solution is being measured, the pump stops and the flow of BHF solution through the tube is stopped.

6. A buffered hydrofluoric acid (BHF) solution concentration measurement method that measures a hydrofluoric acid (HF) concentration in a BHF solution, the BHF solution comprising at least ammonium fluoride ($NH_4F$) and HF in water concentration measurement method comprising:

determining, via a processor, relationships between a pH of the BHF solution and an HF concentration based on the $NH_4F$ concentration of the BHF solution;
measuring a pH value of the BHF solution;
referring to the relationships via the processor; and
calculating, via the processor, the HF concentration from the measured pH value and the referred relationships, wherein
the HF concentration in the BHF solution is between 1 part-per-million (ppm) and 500 ppm.

* * * * *